United States Patent
Edlund

[11] Patent Number: 5,393,325
[45] Date of Patent: * Feb. 28, 1995

[54] COMPOSITE HYDROGEN SEPARATION METAL MEMBRANE

[75] Inventor: David J. Edlund, Redmond, Oreg.

[73] Assignee: Bend Research, Inc., Bend, Oreg.

[*] Notice: The portion of the term of this patent subsequent to Aug. 18, 2009 has been disclaimed.

[21] Appl. No.: 148,999

[22] Filed: Nov. 8, 1993

Related U.S. Application Data

[63] Continuation-in-part of Ser. No. 986,692, Dec. 7, 1992, Pat. No. 5,259,870, which is a continuation-in-part of Ser. No. 566,092, Aug. 10, 1990, abandoned.

[51] Int. Cl.$^6$ ................ B01D 53/22; B01D 71/02
[52] U.S. Cl. ........................... 95/56; 96/11; 55/524
[58] Field of Search ............ 95/55, 56, 524; 96/4, 96/11

[56] References Cited

U.S. PATENT DOCUMENTS

| | | | |
|---|---|---|---|
| 2,958,391 | 11/1960 | deRosset | 95/56 |
| 3,241,298 | 3/1966 | Pierce | 96/11 X |
| 3,336,730 | 8/1967 | McBride et al. | 95/56 |
| 3,344,582 | 10/1967 | Merrill et al. | 95/56 |
| 3,350,846 | 11/1967 | Makrides et al. | 95/56 |
| 3,393,098 | 7/1968 | Hartner et al. | 136/86 |
| 4,388,479 | 6/1983 | Gryaznov et al. | 568/828 |
| 4,468,235 | 8/1984 | Hill | 95/56 X |
| 4,496,373 | 1/1985 | Behr et al. | 95/56 X |
| 4,865,630 | 9/1989 | Abe | 96/11 |
| 4,902,307 | 2/1990 | Gavalas et al. | 95/55 |
| 4,971,696 | 11/1990 | Abe et al. | 96/11 X |
| 5,049,167 | 9/1991 | Castro et al. | 95/55 |
| 5,094,927 | 3/1992 | Baucke et al. | 429/33 |
| 5,139,541 | 8/1992 | Edlund | 95/56 |
| 5,217,506 | 6/1993 | Edlund et al. | 95/56 |
| 5,217,507 | 6/1993 | Spirig | 220/23.6 X |
| 5,259,870 | 11/1993 | Edlund | 95/56 |

FOREIGN PATENT DOCUMENTS

| | | | |
|---|---|---|---|
| 0952442 | 8/1974 | Canada | 95/56 |
| 1058587 | 12/1983 | U.S.S.R. | 96/11 |

OTHER PUBLICATIONS

Hsieh, 33 *Catal Rev. Sci. Eng. I.* (1991).
Sermon et al., 72 *JCS Faraday Trans. I.* 730 (1976).
Gavalas et al., 44 *Chem. Eng. Sci.* 1829 (1989).

*Primary Examiner*—Robert Spitzer
*Attorney, Agent, or Firm*—Chernoff, Vilhauer, McClung & Stenzel

[57] ABSTRACT

Composite hydrogen separation metal membranes are disclosed that contain an intermediate layer separating a base metal and a coating metal, wherein the intermediate layer is not a pure metal or metal alloy and is thermodynamically stable at operating temperatures.

20 Claims, 1 Drawing Sheet

COMPOSITE HYDROGEN SEPARATION METAL MEMBRANE

The government has rights in this invention pursuant to Grant No. ISI-8722212 awarded by the National Science Foundation.

This is a continuation-in-part of application Ser. No. 07/986,692, filed Dec. 7, 1992, now U.S. Pat. No. 5,259,870, which is a continuation-in-part of application Ser. No. 07/566,092, filed Aug. 10, 1990, now abandoned.

BACKGROUND OF THE INVENTION

Hydrogen-permeable membranes are known. They fall generally into three classes: polymeric membranes, inorganic (non-metal porous or nonporous) membranes, and dense (nonporous) metal membranes. Polymeric membranes suffer from limited selectivity toward hydrogen over other gases, and limited resistance to high temperatures and reactive chemicals that may be present in typical feed gases.

Exemplary porous inorganic molecular hydrogen-permeable membranes such as aluminum oxide, silicon oxide, titanium oxide, magnesium oxide, chromium oxide, tin oxide, and various zeolites, have been investigated. See, for example, Hsieh, 33 *Catal. Rev. Sci. Eng.* 1 (1991). While such membranes exhibit very high hydrogen permeability, they also suffer from very low hydrogen selectivity due to their porous nature. Nonporous inorganic oxides are also known to be permeable to hydrogen in its ionic form. For example, U.S. Pat. No. 5,094,927 discloses materials that are permeable to hydrogen ions (referred to as solid-state proton conductors) based on silicon oxide, oxides of Groups IVB, VB, VIB and VIII of the Periodic Table, and fluorides of Groups IIA and IIIB of the Periodic Table. Additionally, diffusion coefficients for hydrogen ions through the oxides of molybdenum and tungsten have been reported by Sermon et al. in 72 *JCS Faraday Trans. I.* 730 (1976). Such solid-state proton conductors have been used by placing them between the cathode and anode in fuel cells, resulting in a net transport of hydrogen between the cathode and anode. However, these solid-state proton conductors are generally brittle and exhibit relatively low permeability to hydrogen, and have not generally been reported for use as a hydrogen separation membrane. The one exception is a nonporous silicon oxide membrane that is reported to allow hydrogen permeation through the silicon oxide by an activated surface-transport mechanism along grain boundaries. See Gavalas et al., 44 *Chem. Eng. Sci.* 1829 (1989). Although this dense silicon oxide membrane exhibits very high selectivities for hydrogen over nitrogen, it is also brittle and susceptible to reaction with steam at elevated temperatures, further limiting its utility.

Dense (nonporous) metal membranes that are selectively permeable to hydrogen are also known. See, for example, U.S. Pat. Nos. 4,388,479 and 3,393,098, both of which disclose Group VIIB and VIII alloy membranes such as palladium alloy catalytic membranes. Such metal membranes are superior to polymeric membranes and to inorganic (non-metal) membranes in that they have essentially complete selectivity for hydrogen over other gases, can be operated at high temperature (up to about 1000° C.), and are chemically resistant to gases in the feed stream. However, the prohibitively high cost of palladium has led to efforts to fabricate composite hydrogen-permeable metal membranes by coating certain less expensive transition metal alloy base metals with palladium or palladium alloys. See, for example, U.S. Pat. Nos. 4,468,235 and 3,350,846. The palladium or palladium-alloy coating on such base metals employs only a relatively small amount of palladium, imparting chemical resistance to the base metal and in some cases increasing the rate of adsorption of hydrogen onto the metal membrane surface. However, such coated metal membranes have an inherent shortcoming in that, under the elevated temperature conditions of use, the coating metal tends to diffuse into the base metal, thereby destroying both the hydrogen permeability and the chemical resistance available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

The use of an intermediate reactive layer to facilitate diffusion bonding of a hydrogen-permeable metal membrane to a substrate metal is known. For example, Russian Patent No. 1,058,587 discloses a method for manufacturing membrane elements for diffusion-based hydrogen separators by diffusion-welding palladium or palladium-alloy membranes to an undefined metal substrate. Specifically, the '587 patent discloses first saturating a hydrogen-permeable coating metal at elevated temperature, then cooling the so-hydrogen-loaded coating metal, then applying a "reactive gasket" of ultra-finely divided powders of metallic oxides over the area between a base metal and the coating metal where the base and coating metals are to be welded together, then subjecting the composite to high pressure (2000–2500 psi) and high temperature (650°–700° C.) to achieve a "diffusion weld" between the coating metal and the base support metal. The diffusion weld results from the complete reduction of the metal oxides "reactive gasket" intermediate layer to pure metal(s) by hydrogen desorbed from the hydrogen-loaded coating metal. It is unclear whether (1) the palladium or palladium-alloy membrane is attached only to the edges of the metal substrate via the diffusion-bonded weld, or (2) the palladium or palladium-alloy membrane completely covers the surface of the metal substrate and the diffusion-bonded weld. In the first case, the welded portion of the membrane need not be hydrogen-permeable as hydrogen is required only to permeate the unwelded portion of the palladium or palladium-alloy membrane and the hydrogen-permeable portion of the membrane is not a composite metal membrane at all, but rather is simply a palladium or palladium-alloy membrane. The drawback of such an approach is that the palladium or palladium-alloy membrane must be sufficiently thick to be self-supporting and the membrane is therefore unacceptably expensive. In the second case, the resulting composite membrane would include an intermediate layer which, after fabrication, is a metal or metal alloy, with attendant reduction in the overall hydrogen permeability of the membrane.

These and other shortcomings of prior art hydrogen-permeable composite metal membranes are overcome by the present invention, which is summarized and described in detail below.

SUMMARY OF THE INVENTION

The present invention comprises a composite hydrogen-permeable, hydrogen-selective, and stable metal membrane and method of using the same for the selective separation of hydrogen from other gases. After fabrication, the essential structure of the membrane comprises a nonporous hydrogen-permeable base metal and a nonporous hydrogen-permeable coating metal separated by a hydrogen-permeable intermediate layer wherein the intermediate layer is not a pure metal or metal alloy, and, at normal operating temperatures and in the presence of hydrogen, is thermodynamically stable in the sense that it will not react with hydrogen or with either the base metal or the coating metal, to form a hydrogen-impermeable layer. Under operating conditions such a composite membrane substantially prevents intermetallic diffusion between the base and coating metals and permits the base metal to retain its hydrogen permeability, which two properties in turn result in higher fluxes and longer membrane lifetimes.

DETAILED DESCRIPTION OF PREFERRED EMBODIMENTS

Figure 1:
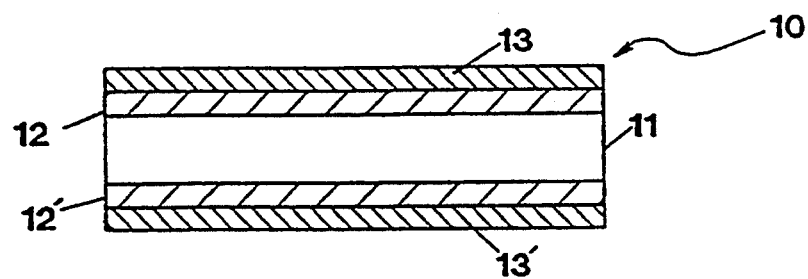
FIG. 1 is a schematic cross-sectional view of an exemplary composite membrane of the present invention.

The overall composite membrane and its component layers are selectively permeable to hydrogen gas and may be used in conventional fashion to separate hydrogen from other gases such as nitrogen, carbon monoxide, carbon dioxide, hydrogen sulfide, steam, ammonia or hydrocarbons such as methane, ethane, propane or olefins, by conventional methods, the essential features of which comprise contacting a feed gas containing hydrogen and other gases at temperatures generally exceeding 400° C. and at a hydrogen partial pressure on the feed side of the membrane that is elevated relative to the hydrogen partial pressure on the permeate side of the membrane, allowing the selective permeation of hydrogen through the composite membrane, and collecting the permeated hydrogen. Since the membrane is selectively permeable to hydrogen even at temperatures <400° C., such as ambient temperature (0° to 50° C.), the membrane has utility for separating hydrogen even at these lower temperatures, subject only to economic limitations since the hydrogen permeability of the membrane is reduced at lower temperatures. Also, the permeate hydrogen need not be collected, but may be burned to water or removed from the permeate side of the membrane with a sweep stream. The composite membrane is also useful in hydrogen separation methods such as are disclosed in commonly-owned U.S. Pat. No. 5,217,506. The hydrogen selectivity of the composite membrane is outstanding, exhibiting a selectivity of $\geq 100$ with a flux of $\geq 0.001$ m$^3$/m$^2$·hr at 500° C. and 100 psig hydrogen feed side pressure with the partial pressure of hydrogen on the permeate side at ambient pressure.

The composite membrane of the present invention is particularly stable under conditions of elevated temperature. Specifically, when exposed to a 100 psig hydrogen feed stream of $\geq 99.95\%$ purity at $\geq 500°$ C., and ambient pressure on the permeate side, the composite membrane retains $\geq 20\%$ of its initial flux over a continuous period of operation of 100 hours at 700° C. and up to 1500 hours at 500° C. As shown herein, this stability is directly attributable to the presence of the intermediate layer.

The base metal of the metal membrane of the present invention is selected from hydrogen-permeable transition metals from Groups IB, IIIB, IVB, VB, VIIB and VIIIB of the Periodic Table; hydrogen-permeable Lanthanide metals; and hydrogen-permeable alloys containing $\geq 20$ wt % of said metals, and may be from 10 to 250 microns in thickness.

The coating metal is a hydrogen-permeable transition metal that is chemically and physically stable at temperatures of at least 400° C., is preferably selected from the transition metals of Groups VIIB and VIIIB of the Periodic Table, most preferably Fe, Mn, Ni, Pd, Pt, Ru and hydrogen-permeable alloys containing $\geq 20$ wt % of said metals, and preferably from 0.01 to 25 microns in thickness.

Since hydrogen must readily diffuse across each layer of the membrane, including the intermediate layer, a key feature of the intermediate layer is that it be formed of a material that will not form a thermodynamically stable material, compound or mixture that is hydrogen-impermeable, by reaction with either the base metal or the coating metal at temperatures in the range of about 400° C. to about 1000° C. By a "thermodynamically stable" material, compound or mixture is meant a material, compound or mixture, the free energy of formation of which is generally less than about 10 Kcal/mole at such temperatures. By "hydrogen-impermeable" is meant a material, compound or mixture that, after formation within the composite metal membrane, results in a substantial decrease in the hydrogen or hydrogen ion permeability of the composite metal membrane relative to its hydrogen or hydrogen ion permeability prior to formation of the hydrogen-impermeable material, compound or mixture. By "substantial decrease" in the hydrogen permeability is meant that the hydrogen or hydrogen ion permeability of the composite metal membrane decreases by more than 80% of its initial value after about 100 hours' operation at 100 psig hydrogen pressure and a temperature above about 400° C. but less than about 1000° C. Specifically, the intermediate layer is thermodynamically stable under operating conditions (temperatures in the 400°–1000° C. range) with respect to reduction of the oxide or sulfide either by hydrogen or by the base metal.

In selecting appropriate materials for use as the intermediate layer it is important to consider the susceptibility of the base metal to form a hydrogen-impermeable layer with the intermediate layer. For instance, the hydrogen-permeable transition metals from Groups IIIB, IVB and VB of the Periodic Table and the Lanthanide metals are much more reactive than are the hydrogen-permeable transition metals of Groups VIIB and VIII of the Periodic Table. Therefore, if the base metal is selected from the former group, exemplary intermediate layers are preferably the oxides of aluminum and silicon. However, if the base metal is selected from Groups VIIB and VIII, exemplary intermediate layers are preferably selected from a broader class, which includes oxides and sulfides of all of the Lanthanide metals, scandium, yttrium, aluminum, silicon, boron, molybdenum, tungsten, vanadium, hafnium and niobium; carbides and nitrides of silicon; carbides, nitrides and silicides of titanium, niobium, vanadium, tantalum, hafnium and zirconium; fluorides of scandium and yttrium; zeolites; graphite; and diamond.

The intermediate layer may be from 0.1 to 300 microns in thickness and is applied as a continuous layer between the coating metal and the base metal and serves not only to prevent contact between the base and coating metals, but also to greatly reduce interdiffusion between the base and coating metals of all chemical elements other than hydrogen. The intermediate layer may be nonporous or porous, provided it meets the other conditions noted above. If it is porous, the mean pore diameter is preferably less than or equal to the thickness of the coating metal layer.

Referring to FIG. 1, there is shown a preferred exemplary embodiment of a five-layer composite metal membrane 10 comprising a base metal layer 11, two microporous intermediate layers 12 and 12' and two coating layers 13 and 13'. Although two layers 12 and 12' and 13 and 13' are shown, the essential three-layer structure of the composite metal membranes of the present invention, having only single layers 12 and 13, also comprises a useful embodiment. Also, the coating layers 13 and 13' may comprise two or more layers.

Figure 2:
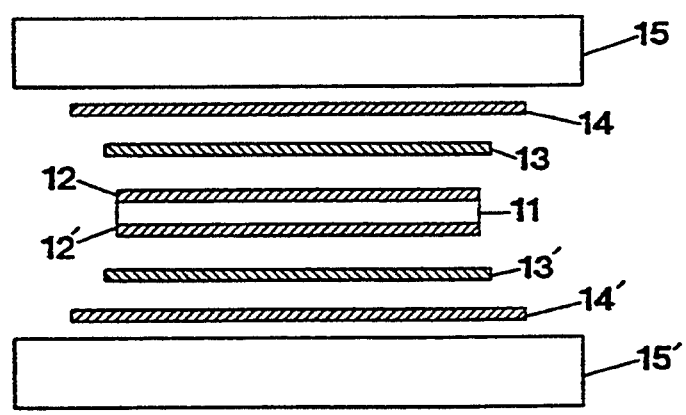
FIG. 2 is a schematic cross-sectional exploded view of an exemplary method of making the composite membrane of the present invention.

Fabrication of the composite metal membranes of the present invention may be accomplished by a variety of methods, including: (1) lamination processes utilizing elevated temperature and pressure, such as hot isostatic pressing; (2) roll cladding; (3) thermal evaporation; (4) chemical- or plasma-vapor deposition; and (5) anodizing or other chemical or electrolytic oxidation methods. FIG. 2 schematically illustrates fabrication by a temperature/pressure lamination technique. In FIG. 2, there is shown an exploded cross-sectional view of the composite metal membrane of FIG. 1 prior to lamination, and wherein like numerals correspond to the same elements. In FIG. 2 there are shown graphite gaskets 14 and 14' and stainless steel press plates 15 and 15'. The graphite gaskets 14 and 14' seal the membrane against exposure to air during the lamination in order to protect against oxidation. The intermediate layer is preferably first applied chemically to the base metal by deposition thereon of an inorganic oxide or sulfide layer. In the case of oxides, the base metal may be coated by spraying, spinning or dipping with a solution of a precursor to the oxide, such as $SiCl_4$ (or $Si(OMe)_4$ with a catalytic amount of concentrated HCl), $WCl_6$ or $MoCl_5$, or alkoxides of Al, La, or Y, which then hydrolyzes to form the oxide layer. Alternatively, an $Al_2O_3$ layer may be formed by anodizing or otherwise chemically or electrolytically oxidizing aluminum. In the case of metal sulfide layers, the base metal may be simply exposed to a sulfide gas, such as hydrogen sulfide, at elevated pressure and temperature for a short time, such as 5 to 15 minutes. Alternatively, the base metal may be coated by spraying, spinning, or dipping with a solution of a precursor to the sulfide, such as $WCl_6$, $MoCl_5$ or $VCl_3$, which may then be reacted with hydrogen sulfide to form the sulfide layer. Yet another method for applying the oxide or sulfide layer is by plasma deposition, or by vapor deposition of the desired oxide or sulfide onto the base metal.

Example 1

A five-layer $Ni/SiO_2/V/SiO_2/Ni$ composite metal membrane comprising a vanadium base metal coated on both sides by $SiO_2$, with both $SiO_2$ layers further coated by a layer of nickel was made using the following procedure. A vanadium disc, 5 cm in diameter and 152 microns thick, served as the base metal, providing good mechanical properties to the composite membrane. Twenty-five-micron-thick nickel foil served as the coating material, providing chemical inertness to the composite membrane.

To fabricate the composite metal membrane, a thin layer of $SiO_2$ was deposited on both sides of the vanadium by dip-coating the vanadium disc with a 1M solution of $SiCl_4$ in methylene chloride at room temperature. As the methylene chloride solvent evaporated, the $SiCl_4$ rapidly hydrolyzed in the presence of atmospheric moisture to yield a film of $SiO_2$ approximately 25 microns thick. Good adhesion between the $SiO_2$ layer and the vanadium was observed. Next, the $SiO_2$-coated vanadium was laminated with the nickel foil at 700° C. under 20,000 pounds of pressure for 4 hours as shown schematically in FIG. 2 to produce the composite membrane. The composite membrane so prepared was flexible, and showed no sign of delamination when bent.

Average hydrogen flux through the composite membrane was measured at 700° C. using a 99.999% pure hydrogen gas feed stream at 100 psig (780 kPa), the permeated hydrogen being at ambient pressure. For comparison, the average hydrogen flux through a control three-layer membrane made by laminating the same thickness of nickel foil directly to the same thickness of vanadium without the use of an intervening $SiO_2$ layer was measured under identical conditions. The resulting average hydrogen flux in units of $m^3/m^2 \cdot hr$ are given in the table below for the initial flux and after 50 hours of operation.

| Membrane | Flux (initial) | Flux (50 hrs) | % Initial Flux |
|---|---|---|---|
| 5-layer | 0.9 | 0.6 | 67 |
| 3-layer | 0.15 | 0.006 | 4 |

For this five-layer composite membrane, the layer that has the greatest resistance to hydrogen permeation (i.e., the layer that has the lowest hydrogen permeability) is the thin nickel coating (the limiting hydrogen flux through a nickel membrane 5 cm in diameter and 25 microns thick is 0.9 $m^3/m^2 \cdot hr$). Since the observed rate of hydrogen permeation through the composite membrane cannot exceed the rate of permeation through each chemically distinct layer of the membrane, the nickel coating of the $Ni/SiO_2/V/SiO_2/Ni$ membrane limits the overall hydrogen flux.

As this Example shows, the five-layer composite metal membrane having intermediate $SiO_2$ layers shows higher flux and longer lifetime (retaining 67% of the initial flux) than the three-layer control membrane having no intermediate $SiO_2$ layer, indicating that the $SiO_2$ intermediate layer is effective at preventing excessive decline in hydrogen flux.

Example 2

A seven-layer $Ni/Cu/SiO_2/V/SiO_2/Cu/Ni$ composite metal membrane was made as follows. A vanadium disc, 5 cm in diameter and 152 microns thick, served as the base metal. A two-layer Ni/Cu foil 31 microns thick (made by laminating a 6-micron Ni foil to a 25-micron Cu foil) served as the coating material, providing chemical inertness to the composite membrane. A thin (≦25 microns) layer of $SiO_2$ between the vanadium and the Ni/Cu coating served as the intermediate layer, and was deposited on both sides of the vanadium by spin coating the vanadium with a 1M solution of $Si(OMe)_4$ in methanol containing a catalytic amount of concentrated HCl. The $SiO_2$-coated vanadium was laminated with the Ni/Cu foil in substantially the same manner as in Example 1, with the Cu side facing the $SiO_2$ layer.

Average hydrogen flux through the so-fabricated composite membrane was measured in the same manner as in Example 1. For comparison, the average hydrogen flux through a five-layer control membrane made by laminating the same thickness of Ni/Cu foil directly to the same thickness of vanadium without the use of an intervening $SiO_2$ layer was measured under identical conditions. The results are given in the table below after 72 hours of operation.

| Membrane | Flux (initial) | Flux (72 hrs) | % Initial Flux |
|---|---|---|---|
| 7-layer | 2.4 | 2.4 | 100 |
| 5-layer | 0.6 | 0.06 | 10 |

As is apparent, the seven-layer composite metal membrane having the $SiO_2$ intermediate layer between the Cu and V layers showed higher flux and more stable hydrogen flux than the five-layer control membrane having no intermediate $SiO_2$ layers.

Example 3

A five-layer Ni/V-sulfide/V/V-sulfide/Ni composite metal membrane was made as follows. A vanadium disc, 5 cm in diameter and 152 microns thick, served as the base metal, while a 6-micron-thick Ni foil served as the coating material. A thin layer of vanadium sulfide served as the intermediate layer, which was formed on both sides of the vanadium by exposing the vanadium disc to 30 psig $H_2S$ at 700° C. for 10 minutes. Good adhesion between the vanadium sulfide layer and the vanadium was observed. The vanadium sulfide-coated vanadium was then laminated with the Ni foil at 700° C. under 20,000 pounds of pressure for 4 hours.

The average hydrogen flux through the composite membrane was measured in the same manner as in Example 1 and compared with the average hydrogen flux through a three-layer control membrane made by laminating the same thickness of Ni foil directly to the same thickness of vanadium under identical conditions without the use of an intervening sulfided-vanadium layer. The results after 50 hours of operation are given in the table below.

| Membrane | Flux (initial) | Flux (50 hrs) | % Initial Flux |
|---|---|---|---|
| 5-layer | 0.062 | 0.046 | 74 |
| 3-layer | 0.14 | 0.004 | 3 |

As is apparent, although the five-layer composite membrane with the V-sulfide intermediate layers initially showed relatively lower hydrogen flux, after 50 hours it showed more than 10 times the hydrogen flux of the three-layer Ni/V/Ni control membrane having no corresponding intermediate layers. (The flux through the five-layer composite membrane of this Example was less than that of Example 1 due to the lower hydrogen permeability of the sulfide intermediate layer relative to the $SiO_2$ layer.)

Example 4

A five-layer $Pd/SiO_2/V/SiO_2/Pd$ composite metal membrane was made as follows. A vanadium disc, 5 cm in diameter and 30 microns thick, served as the base metal, while a 25-micron-thick palladium foil served as the coating material. A thin layer of $SiO_2$ served as the intermediate layer. The $SiO_2$ layer was deposited on one surface of each of two 5-cm-diameter pieces of Pd foil by first placing a thin film of methanol containing a catalytic amount of HCl on the surfaces of the Pd, then, before the methanol/HCl evaporated, adding $Si(OMe)_4$ dropwise until each of the Pd surfaces was entirely covered; this yielded a thin (≦25-micron) $SiO_2$ layer by hydrolysis of the $Si(OMe)_4$ due to reaction with atmospheric moisture. The two pieces of $SiO_2$-coated Pd foil were placed $SiO_2$ layer down on both sides of the vanadium disc. The entire assembly was then placed directly in a permeation test cell and laminated in situ during permeation testing at 700° C. using the gas feed-pressure of 100 psig (780 kPa) to achieve lamination. The average hydrogen flux through the composite membrane was measured under the same conditions as in Example 1 for nearly six hours and was observed to have stabilized after about two hours at 25.3 $m^3/m^2$·hr. This high flux is a result of using palladium as the coating metal, rather than nickel or nickel/copper alloy, which has a greater permeability to hydrogen than do nickel or nickel/copper alloys. Even after 50 hours' operation, the flux through the membrane remained constant at 25.3 $m^3/m^2$·hr, demonstrating that the membrane retained 100% of the initial flux.

For comparison, the average hydrogen flux through a three-layer control membrane made by laminating the same thickness of palladium foil directly to the same thickness of vanadium foil without the use of an intervening $SiO_2$ layer was measured under identical conditions. The flux through this three-layer control membrane decreased steadily from its initial value of 19 $m^3/m^2$·hr to 14 $m^3/m^2$·hr after 6 hours, then to 0.91 $m^3/m^2$·hr after 50 hours' operation, demonstrating that without the intermediate $SiO_2$ layer the membrane retained only 5% of its initial flux. As is also apparent, the five-layer composite membrane exhibited higher average flux than did the control membrane.

| Membrane | Flux (initial) | Flux (50 hrs) | % Initial Flux |
|---|---|---|---|
| 5-layer | 25.3 | 25.3 | 100 |
| 3-layer | 19 | 0.91 | 5 |

Example 5

To demonstrate high permeability of the $SiO_2$ layer, a three-layer $Pd/SiO_2/Pd$ composite metal membrane was made. Palladium served as the coating metal and the base metal was omitted. Palladium foil, 5 cm in diameter and 25 microns thick, was coated on one side with a thin layer of $SiO_2$ as in Example 4. Another piece of palladium foil of the same dimensions was then placed over the $SiO_2$-coated palladium so that the $SiO_2$ layer was between the two palladium foils. The assembly was then placed in a permeation test cell and laminated in situ as in Example 4. The average hydrogen flux through the composite membrane, measured under the same conditions as in Example 1, was 31 m$^3$/m$^2$·hr.

Example 6

To demonstrate the high permeability of a WO$_3$ layer for use as an intermediate layer, a three-layer Pd/WO$_3$/Pd composite metal membrane was made. Palladium served as the coating metal and the base metal was omitted. Palladium foil, 5 cm in diameter and 25 microns thick, was coated on one side with a thin layer of WO$_3$ by applying to one surface a dilute solution of WCl$_6$ in a mixture comprising about 94% methylene chloride, about 5% acetonitrile, and about 1% Si(OMe)$_4$. The Si(OMe)$_4$, upon hydrolysis to SiO$_2$, serves as a binder to produce a more uniform coating of WO$_3$. The WCl$_6$ rapidly hydrolyzed in the presence of atmospheric moisture to yield a thin film of WO$_3$. Another piece of palladium foil of the same dimensions was then placed over the WO$_3$-coated palladium so that the WO$_3$ layer was between two layers of palladium. The assembly was then placed in a permeation test cell and laminated in situ as in Example 4. The average hydrogen flux through the composite membrane was measured under the same conditions as in Example 1 and was observed to be 42 m$^3$/m$^2$·hr.

Example 7

To demonstrate the high permeability of a MoO$_3$ layer for use as an intermediate layer, a three-layer Pd/MoO$_3$/Pd composite metal membrane similar to that of Examples 5 and 6 was made as follows. Palladium foil, 5 cm in diameter and 25 microns thick, was coated on one side with a thin layer of MoO$_3$ by applying to one surface a solution of MoCl$_5$ in the same solvent mixture as in Example 6. The MoCl$_5$ rapidly hydrolyzed in the presence of atmospheric moisture to yield a thin film of MoO$_3$. Another piece of palladium foil of the same dimensions was then placed over the MoO$_3$-coated palladium so that the MoO$_3$ layer was between the two pieces of palladium. The assembly was then placed in a permeation test cell and laminated in situ as in Example 4. The average hydrogen flux through the composite membrane was measured under the same conditions as in Example 1 and was observed to be 67 m$^3$/m$^2$·hr.

Example 8

A five-layer Ni/MoO$_3$/Cu/MoO$_3$/Ni composite metal membrane was made as follows. A copper disc, 5 cm in diameter and 250 microns thick, served as the base metal, while a 25-micron-thick nickel foil served as the coating material. A thin layer of MoO$_3$ served as the intermediate layer, and was deposited on one surface of each of two pieces of 5-cm-diameter nickel foil as in Example 7. The two pieces of MoO$_3$-coated nickel foil were placed with the MoO$_3$ side adjacent the two sides of the copper foil. The entire assembly was then placed directly in a permeation test cell and laminated in situ during permeation testing as in Example 4. Average hydrogen flux under the same conditions as in Example 1 through the composite membrane was measured at 0.37 m$^3$/m$^2$·hr. This flux is identical to that through a copper membrane (250 microns thick, 5 cm diameter) under the same conditions of temperature and hydrogen pressure. As expected, the copper base metal layer limits the overall flux through this composite membrane.

Example 9

A five-layer Pd/Y$_2$O$_3$/V/Y$_2$O$_3$/Pd composite metal membrane was made using the following procedure. Vanadium foil 25 μm in thickness served as the base metal, while palladium foil of the same thickness served as the coating metal. A thin layer of Y$_2$O$_3$ was deposited on both sides of the vanadium foil by dropwise addition of an aqueous/methanolic solution containing yttrium isopropoxide [Y(OC$_3$H$_6^i$)$_3$] in toluene with HCl as a hydrolysis-promoting catalyst. The Y(OC$_3$H$_6^i$)$_3$ rapidly hydrolyzed in a 70% relative humidity chamber, forming a thin coating on the vanadium. Liberation of excess solvent and condensation of hydroxides to oxides was achieved by heating, under a flow of Argon, the so-coated vanadium foil at 450° C. for one hour. The resulting Y$_2$O$_3$-coated vanadium foil was covered with Pd and laminated in situ under 100 psig (780 kPa) Argon at 700° C. for two hours.

Hydrogen flux was measured for 13 days through this five-layer composite membrane. Average hydrogen flux was 16 m$^3$/m$^2$·hr, measured under the same conditions as in Example 1, and the membrane maintained 100% of its initial flux. These data indicate that the Y$_2$O$_3$ layer imparts membrane stability as compared to the Pd/V membrane having no intermediate layer and as compared to a NiO-containing five-layer Pd/NiO/V/NiO/Pd membrane (see Comparative Example below).

Example 10

To demonstrate the advantages deriving from a porous hydrogen-permeable intermediate layer, a five-layer Pd/Al$_2$O$_3$/V/Al$_2$O$_3$/Pd composite metal membrane was made as follows. A vanadium disc, 2.9 cm in diameter and 30 microns thick, served as the base metal, while 25-micron-thick palladium foil served as the coating metal. Alumina paper with 79% porosity (APA-3 from Zircar Products of New York, N.Y.) served as the intermediate layer. The alumina, 2.9 cm in diameter and 0.03 cm thick, was placed on both sides of the vanadium disk. Palladium foil with a diameter of 3.8 cm was then used to cover the exposed alumina. The composite metal membrane was assembled in a test cell and then laminated in situ at 500° C. using an argon gas feed pressure of 100 psig (780 kPa).

Average hydrogen flux through the composite membrane was measured at 500° C. using a 99.95% pure hydrogen gas feed stream at 100 psig (780 kPa), the permeated hydrogen being at ambient pressure. The initial hydrogen flux was 11.2 m$^3$/m$^2$·hr. After 1500 hours of operation, the hydrogen flux was 11.1 m$^3$/m$^2$·hr, representing 99% of the original flux.

For comparison, the average hydrogen flux through a three-layer Pd/V/Pd control membrane made by laminating the same thickness of palladium foil directly to the same thickness of vanadium foil without the use of the intervening alumina layer was measured under identical conditions. The flux through this control membrane decreased steadily from its initial value of 5.3 m$^3$/m$^2$·hr to 1.7 m$^3$/m$^2$·hr after 140 hours of operation, demonstrating that without the intermediate alumina layer the membrane retained only 32% of its initial flux. As is also apparent, the flux through the three-layer control membrane was less than one-half the flux of the five-layer composite membrane.

Example 11

Another five-layer composite membrane (Pd-5Ru/Al$_2$O$_3$/V/Al$_2$O$_3$/Pd-5Ru) having a porous hydrogen-permeable intermediate layer was prepared in substantially the same manner as in Example 10 with the exceptions that the alumina layer was formed from alumina filter disks about 70 microns thick and having a 0.02 micron pore rating (Anodisc 47 from Whatman Scientific of Maidstone, England), while 25-micron-thick Pd-5Ru foil served as the coating metal. (Pd-5Ru is an alloy of Pd containing about 5% Ru.)

Average hydrogen flux through the five-layer composite membrane was measured in the same manner as in Example 10. The average initial hydrogen flux was 9.8 m$^3$/m$^2$·hr. After 400 hours of operation, the hydrogen flux was 9.7 m$^3$/m$^2$·hr, representing 98% of the original flux.

Example 12

Substantially the same five-layer composite membrane of Example 11 was fabricated, with the exception that the alumina layer was of the same material as in the membrane of Example 10. Average hydrogen flux through this membrane was measured at 600° C. but otherwise in the same manner as in Example 10. The initial hydrogen flux was 15.5 m$^3$/m$^2$·hr. After nearly 500 hours of operation, the hydrogen flux was still 15.5 m$^3$/m$^2$·hr, representing no decline from the original flux.

Example 13

Substantially the same five-layer composite membrane of Example 11 was fabricated, with the exception that the alumina layer comprised alumina cloth (ALK-15 from Zircar Products) with 50–80% porosity, 2.9 cm in diameter and about 0.03 cm thick. Average hydrogen flux through this membrane was measured in the same manner as in Example 12. The initial hydrogen flux was 18.5 m$^3$/m$^2$·hr. After nearly 200 hours of operation, the hydrogen flux was 17.8 m$^3$/m$^2$·hr, representing 96% of the original flux.

Comparative Example

A five-layer Pd/NiO/V/NiO/Pd composite metal membrane was made as follows. Vanadium foil 25 μm thick served as the base metal, while Pd foil of the same thickness served as the coating metal. A thin layer of Ni(OH)$_2$ was deposited on both sides of the vanadium from a suspension of Ni(OH)$_2$ in a basic (pH=12) aqueous solution. The vanadium foil/Ni(OH)$_2$ coating was heated at 450° C. in an Argon atmosphere, condensing hydroxide to oxide and liberating excess water. Each side of the coated foil was covered with the Pd foil and laminated in situ under 100 psig (780 kPa) Argon at 700° C. for two hours.

Average hydrogen flux through the five-layer composite membrane was measured in the same manner as in Example 1. The initial hydrogen flux was 11.3 m$^3$/m$^2$·hr. After operating for nearly four days, the flux had decreased to 0.6 m$^3$/m$^2$·hr, representing 5% of the initial flux. This result indicates that the use of NiO as the intermediate layer yields a membrane that does not exhibit stable hydrogen flux. Indeed, this composite metal membrane is seen to be no more stable with respect to hydrogen flux than the same membrane without the intermediate NiO layer (see Example 4).

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A hydrogen separation composite metal membrane which, after fabrication, comprises a nonporous hydrogen-permeable base metal and a nonporous hydrogen-permeable coating metal separated by a hydrogen-permeable intermediate layer, wherein said intermediate layer is not a pure metal or metal alloy, and at a temperature of from about 400° C. to about 1000° C. does not form a thermo-dynamically stable hydrogen-impermeable layer by reaction with hydrogen or by reaction with said base metal or with said coating metal.

2. The membrane of claim 1 wherein said base metal is selected from hydrogen-permeable Lanthanide metals; hydrogen-permeable transition metals from Groups IB, IIIB, IVB, VB, VIIB and VIIIB of the Periodic Table; and hydrogen-permeable alloys containing ≧20 wt % of said metals.

3. The membrane of claim 1 wherein said coating metal is selected from a hydrogen-permeable transition metal and a hydrogen-permeable alloy thereof, said coating metal being chemically and physically stable at temperatures of at least 400° C.

4. The membrane of claim 3 wherein said coating metal is selected from the group consisting essentially of the transition metals from Groups VIIB and VIIIB of the periodic table, and alloys containing ≧20 wt % of said metals.

5. The membrane of claim 4 wherein said coating metal is selected from the group consisting essentially of Fe, Mn, Ni, Pd, Pt and Ru.

6. The membrane of claim 1 wherein said intermediate layer is microporous.

7. The membrane of claim 1 wherein said intermediate layer is aluminum oxide.

8. The membrane of claim 1 wherein said intermediate layer is lanthanum oxide.

9. The membrane of claim 1 wherein said intermediate layer is molybdenum oxide.

10. The membrane of claim 1 wherein said intermediate layer is silicon oxide.

11. The membrane of claim 1 wherein said intermediate layer is tungsten oxide.

12. The membrane of claim 1 wherein said intermediate layer is yttrium oxide.

13. The membrane of claim 1 wherein said intermediate layer is vanadium sulfide.

14. The membrane of claim 1 wherein said base metal is vanadium; said coating metal is selected from palladium and platinum and alloys thereof; and said intermediate layer is porous aluminum oxide.

15. The membrane of claim 1 wherein said base metal is vanadium and said coating metal is an alloy comprising 20 wt % nickel and 80 wt % copper.

16. The membrane of claim 1 wherein said base metal is vanadium and said coating metal is palladium.

17. The membrane of claim 1 wherein said base metal is vanadium and said coating metal is nickel.

18. The membrane of claim 1 wherein said base metal is vanadium and said coating metal is platinum.

19. A method for separating hydrogen from other gases comprising contacting a gaseous feed stream containing hydrogen with the membrane of claim 1 at a hydrogen partial pressure on the feed side of said membrane that is elevated relative to the hydrogen partial pressure on the permeate side of said membrane, allowing the selective permeation of hydrogen through said membrane, and separating hydrogen that permeates through said membrane.

20. The method of claim 19 wherein the temperature is at least 400° C.

* * * * *